(12) United States Patent
Benet Buchholz et al.

(10) Patent No.: US 9,428,462 B2
(45) Date of Patent: Aug. 30, 2016

(54) 4-[-2-[[5-METHYL-1-(2-NAPHTHALENYL)-1H-PYRAZOL-3-YL]OXY]ETHYL] MORPHOLINE HYDROCHLORIDE AMORPHOUS SOLID FORMS (75) Inventors: Jordi Benet Buchholz, Altafulla-Tarragona (ES); Laura Puig Fernandez, Saragossa (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 0 days.

(21) Appl. No.: 13/816,194

(22) PCT Filed: Aug. 8, 2011

(86) PCT No.: PCT/EP2011/063583
§ 371 (c)(1),
(2), (4) Date: Feb. 25, 2013

(87) PCT Pub. No.: WO2012/019984
PCT Pub. Date: Feb. 16, 2012

(65) Prior Publication Data
US 2013/0150575 A1   Jun. 13, 2013

(30) Foreign Application Priority Data
Aug. 9, 2010   (EP) .................... 10382225

(51) Int. Cl.
C07D 231/22   (2006.01)
C07D 413/12   (2006.01)

(52) U.S. Cl.
CPC ................. *C07D 231/22* (2013.01)

(58) Field of Classification Search
CPC ................................... C07D 231/22
USPC ............................................... 544/140
See application file for complete search history.

(56) References Cited

U.S. PATENT DOCUMENTS

| | | | |
|---|---|---|---|
| 7,696,199 B2* | 4/2010 | Laggner et al. | 514/227.8 |
| 8,293,740 B2* | 10/2012 | Laggner et al. | 514/235.8 |
| 8,314,096 B2* | 11/2012 | Laggner et al. | 514/231.5 |
| 8,470,867 B2* | 6/2013 | Laggner et al. | 514/407 |
| 8,492,425 B2* | 7/2013 | Torrens Jover et al. | 514/407 |
| 2008/0125416 A1 | 5/2008 | Laggner et al. | |
| 2010/0081659 A1* | 4/2010 | Laggner | 514/236.5 |
| 2010/0240711 A1 | 9/2010 | Takada et al. | |
| 2012/0141606 A1* | 6/2012 | Baeyens-Cabrera et al. | 424/649 |
| 2012/0283262 A1* | 11/2012 | Soler Ranzani et al. | 514/236.5 |
| 2012/0302568 A1* | 11/2012 | Vela Hernandez et al. | 514/236.5 |
| 2012/0316336 A1* | 12/2012 | Berenguer Maimo et al. | 544/140 |
| 2013/0109692 A1* | 5/2013 | Vela Hernandez et al. | 514/236.5 |
| 2013/0143884 A1* | 6/2013 | Cuberes-Altisent et al. | 514/236.5 |
| 2013/0158033 A1* | 6/2013 | Vela Hernandez et al. | 514/236.5 |
| 2013/0324535 A1* | 12/2013 | Zamanillo-Castanedo et al. | 514/236.5 |

FOREIGN PATENT DOCUMENTS

| | | | |
|---|---|---|---|
| EP | 2 116 539 A1 | | 11/2009 |
| EP | 2361904 A1 | | 8/2011 |
| EP | 2426112 A1 | | 3/2012 |
| JP | H4(1992)-364129 | | 12/1992 |
| JP | 2008-510767 | | 4/2008 |
| WO | WO 2006021462 A1 * | | 3/2006 |
| WO | WO 2009/038112 | | 3/2009 |

OTHER PUBLICATIONS

International Search Report issued in priority International Patent Application No. PCT/EP2011/063583 on Aug. 31, 2011.
Hanner et al., "Purification, molecular cloning, and expression of the mammalian sigma$_1$-binding site," Proc. Natl. Acad. Sci. USA vol. 93 pp. 8072-8077 (1996).
Lang et al., "The Use of Polymer Heteronuclei for Crystalline Polymorph Selection," J. Am. Chem. Soc. vol. 124 pp. 14834-14835 (2002).
Price et al., "Crystalline Polymorph Selection and Discovery with Polymer Heteronuclei," J. Am. Chem. Soc. vol. 127 pp. 5512-5517 (2005).
Quiron et al., "A proposal for the classification of sigma binding sites," Trends in Pharmacol. Sci. vol. 13 pp. 85-86 (1992).
Snyder et al., "Receptor Mechanisms in Antipsychotic Drug Action: Focus on Sigma Receptors," Journal of Neuropsychiatry vol. 1 No. 1 pp. 7-15 (1989).

(Continued)

*Primary Examiner* — Nyeemah A Grazier
(74) *Attorney, Agent, or Firm* — Jenkins, Wilson, Taylor & Hunt, P.A.

(57) ABSTRACT

The present invention relates to solid forms having a low degree of crystallinity or substantially amorphous of the hydrochloride salt of 4-[2-[[5-methyl-1-(2-naphthalenyl)-1H-pyrazol-3-yl]oxy]ethyl]morpholine (P027) and processes for their preparation.

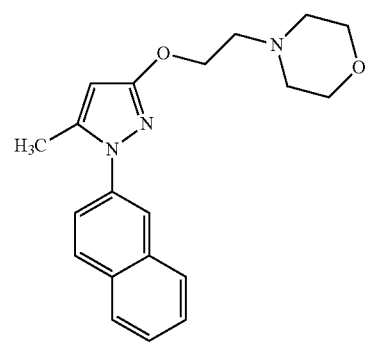

10 Claims, 3 Drawing Sheets

(56) References Cited

OTHER PUBLICATIONS

Walker et al., "Sigma Receptors: Biology and Function," Pharmacological Reviews vol. 42 No. 4 pp. 355-401 (1990).
Anderson and Flora, "Preparation of Water-Soluble Compounds Through Salt Formation," in Practice of Medicinal Chemistry, last volume, Academic Press Limited, pp. 739-754 (1996).
Haleblian, "Characterization of Habits and Crystalline Modification of Solids and Their Pharmaceutical Applications," Journal of Pharmaceutical Sciences, vol. 64, No. 8 pp. 1269-1288 (1975).
Hancock and Zografi, "Characteristics and Significance of the Amorphous State in Pharmaceutical Systems," Journal of Pharmaceutical Sciences, vol. 86, No. 1 pp. 1-12 (1997).
Official Action corresponding to Japanese Patent Application No. 2013-523580, mailed Mar. 31, 2015.

* cited by examiner

4-[-2-[[5-METHYL-1-(2-NAPHTHALENYL)-1H-PYRAZOL-3-YL]OXY]ETHYL] MORPHOLINE HYDROCHLORIDE AMORPHOUS SOLID FORMS

CROSS-REFERENCE TO RELATED APPLICATIONS

This application is filed under the provisions of 35 U.S.C. §371 and claims the priority of International Patent Application No. PCT/EP2011/063583 filed on Aug. 8, 2011, and of European Patent Application No. 10382225.0 filed on Aug. 9, 2010. The disclosures of the foregoing international patent application and European patent application are hereby incorporated by reference herein in their respective entireties.

FIELD OF THE INVENTION

The present invention relates to solid forms having a low degree of crystallinity, and to substantially amorphous forms, of the hydrochloride salt of 4-[2-[[5-methyl-1-(2-naphthalenyl)-1H-pyrazol-3-yl]oxy]ethyl]morpholine (P027) and processes for their preparation.

BACKGROUND

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some naroleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands. 4-[2-[[5-methyl-1-(2-naphthalenyl)-1H-pyrazol-3-yl]oxy]ethyl]morpholine is one of such promising sigma receptor ligands. The compound and its synthesis are disclosed and claimed in WO2006/021462.

4-[2-[[5-methyl-1-(2-naphthalenyl)-1H-pyrazol-3-yl]oxy]ethyl]morpholine is a highly selective sigma-1 (σ-1) receptor antagonist. It has displayed strong analgesic activity in the treatment and prevention of chronic and acute pain, and particularly, neuropathic pain. The compound has a molecular weight 337.42 uma. The structural formula of the compound is:

The solid state physical properties of a pharmaceutical compound can be influenced by the conditions under which the compound is obtained in solid form. Solid state physical properties include, for example, the flowability of the milled solid which affects the ease with which the compound is handled during processing into a pharmaceutical product. Another important solid state property of a pharmaceutical compound is its rate of dissolution in aqueous fluid. The rate of dissolution of an active ingredient in a patient's stomach fluid can have therapeutic consequences because it imposes an upper limit on the rate at which an orally administered active ingredient can reach the blood. The solid-state form of a compound may also affect its solubility, bioavailability, behavior on compaction, stability, or its electrostatic nature.

Polymorphism is the property of some molecules and molecular complexes to assume more than one crystalline or amorphous form in the solid state. In general, polymorphism is caused by the ability of the molecule of a substance to change its conformation or to form different inter molecular and intramolecular interactions, particularly hydrogen bonds, which is reflected in different atom arrangements in the crystal lattices of different polymorphs. Accordingly, polymorphs are distinct solids sharing the same molecular Formula, having distinct advantageous and/or disadvantageous physical properties compared to other forms in the polymorph family.

The discovery of new crystalline polymorphic or amorphous forms of a pharmaceutical compound provides an opportunity to improve the physical or performance characteristics of a pharmaceutical product in that it enlarges the repertoire of materials that a formulation scientist has available for designing, for example, a pharmaceutical dosage form of a drug with a targeted release profile or other desired characteristics.

The polymorph phase I of the hydrochloride salt of 4-[2-[[5-methyl-1-(2-naphthalenyl)-1H-pyrazol-3-yl]oxy]

ethyl]morpholine (P027) and its synthesis are disclosed and claimed in the co-pending application EP 10382025.4 filed on Feb. 4, 2010. Said polymorph phase I has found to be highly stable over the time with good flow and dissolution characteristics, thus providing advantageous production, handling, storage and therapeutic properties.

Other solid forms of the P027 compound are described in the co-pending application EP10382226.8 filed at the same time as the present one and not published.

Nevertheless, to carry out its pharmaceutical development and release its potential, there is a need in the art for additional solid forms of 4-[2-[[5-methyl-1-(2-naphthalenyl)-1H-pyrazol-3-yl]oxy]ethyl]morpholine that will facilitate the preparation of better formulations of this active pharmaceutical ingredient. In this regard, alternative morphological forms of the compound may have widely different properties and could either become intermediates for other forms (e.g. the highly stable form I above-mentioned) or provide in themselves a still better formulation of this active pharmaceutical ingredient. Thus it is important to find such forms, having desirable properties for pharmaceutical use.

BRIEF DESCRIPTION OF THE INVENTION

The inventors of the present invention have surprisingly found and demonstrated that new solid forms of the hydrochloride salt of 4-[2-[[5-methyl-1-(2-naphthalenyl)-1H-pyrazol-3-yl]oxy]ethyl]morpholine (P027) may achieve one or more of the above mentioned objectives. The novel amorphous form of P027 herein disclosed is stable over the time, has good flow and dissolution characteristics and notably may be useful as intermediate for other forms such as the crystalline form I of P027. In addition, they can be obtained through different procedures and conditions.

Thus, the present invention relates to both substantially amorphous forms of P027 and forms of P027 having low degrees of crystallinity as well as several processes for their preparation.

In one embodiment, the present invention is directed to a solid form of the hydrochloride salt of 4-[2-[[5-methyl-1-(2-naphthalenyl)-1H-pyrazol-3-yl]oxy]ethyl]morpholine having a degree of crystallinity below about 10%, below about 20% or below about 30%.

In another embodiment, the present invention is directed to a substantially amorphous form of the hydrochloride salt of 4-[2-[[5-methyl-1-(2-naphthalenyl)-1H-pyrazol-3-yl]oxy]ethyl]morpholine.

Preferably, said amorphous form of P027 has a FTIR spectrum showing characteristic peaks at about: 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819 and 748 $cm^{-1}$.

The preparation of the solid forms of P027, amorphous or with low crystallinity, represents additional embodiments of the present invention. These solid forms of P027 may be obtained by solvent evaporation using a suitable solvent or mixture of solvents.

The solid forms of P027 may be also obtained in polymer induced crystallizations by:
  solvent evaporation;
  antisolvent addition; or
  crystallization from hot saturated solutions.

Preferably, the solvent used in the above processes is water, acetonitrile, isopropanol, methanol or mixtures comprising water.

Another embodiment of the present invention includes the transformation of a P027 solid form having a low degree of crystallinity, including substantially amorphous forms, into a more stable polymorphic form such as phase I form.

A further embodiment of the present invention includes pharmaceutical compositions comprising the above-mentioned solid forms of the hydrochloride salt of 4-[2-[[5-methyl-1-(2-naphthalenyl)-1H-pyrazol-3-yl]oxy]ethyl]morpholine.

These aspects and preferred embodiments thereof are additionally also defined in the claims.

DETAILED DESCRIPTION OF THE INVENTION

The inventors of the present invention have found a novel form, concretely an amorphous form, of the hydrochloride salt of 4-[2-[[5-methyl-1-(2-naphthalenyl)-1H-pyrazol-3-yl]oxy]ethyl]morpholine (P027) which provides advantageous production, handling, storage and therapeutic properties. The novel P027 compound amorphous form is stable over the time and has good flow and dissolution characteristics and can be formulated and administered providing stable compositions and good pharmacological properties. Additionally, the amorphous form of P027 may be used for obtaining other forms, such as crystalline phase I form of P027.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, "room temperature" or its abbreviation "rt" is taken to mean 20 to 25° C.

The P027 amorphous form obtained was characterized by powder X-ray diffraction (PXRD), proton nuclear magnetic resonance ($^1$H-NMR), differential scanning calorimetry (DSC), thermogravimetric analysis (TGA) and Fourier-transformed infrared spectroscopy. The present invention is directed in one aspect to the P027 amorphous form in itself, regardless of the technique used for its characterization. Therefore, the techniques and results provided herein are not intended to limit the present invention, but to serve as characterization of the same. The skilled person will be able, given the guidance and results described herein, to compare and characterize using the available techniques a amorphous phase of the compound 4-[2-[[5-methyl-1-(2-naphthalenyl)-1H-pyrazol-3-yl]oxy]ethyl]morpholine hydrochloride (P027).

As mentioned, the present invention encompasses both substantially amorphous forms of P027 and forms of P027 having low degrees of crystallinity. Low degrees of crystallinity include a crystallinity below about 10%, below about 20% or below about 30%. The degree of crystallinity may be calculated according to the method described in WO97/41114 with powder X-ray diffraction (XRD), as follows: A thin layer of the triturated sample is smeared onto a cut silicon single crystal zero background holder which is rotated during the measurement. Cu Kα radiation and constant or automatic antiscatter and divergence slits were used to obtain a diffractogram from 1 or 2° 2θ to at least 35°. The % crystallinity is calculated with the formula:

% crystallinity=100*C/(A+C)

C=the area from the peaks in the diffractogram ("the crystalline area"),

A=the area between the peaks and the background ("the amorphous area").

The expression "substantially amorphous form" refers to a form which does not show peaks at the PXRD pattern i.e. a form having a degree of crystallinity equal to about 0%.

The preparation of solid samples of compound P027 was performed in a set of 40 solvents (table 1). Solvents were selected according to previous experience with the aim to cover a broad range of properties.

TABLE 1

Solvents used in the formation of P027 solid forms

| Name | Code | Name | Code |
|---|---|---|---|
| Dimethylsulfoxide | DMS | Diethoxymethane | DEM |
| N,N-Dimethylacetamide | DMA | 1,2-Dichloroethane | DCE |
| N,N-Dimethylformamide | DMF | Isopropanol | IPH |
| Xylene | XIL | Acetonitrile | ACN |
| Chlorobenzene | CLB | Cyclohexane | CHE |
| n-Butanol | NBL | Methyl ethyl ketone | MEC |
| Methyl isobutyl ketone | MIC | Butyl amine | BUA |
| Isobutyl acetate | AIB | Ethanol | EOH |
| Pyridine | PYR | Ethyl acetate | AET |
| Toluene | TOL | 1,1,1-Trichloroethane | TCE |
| 3-Pentanone | POA | n-Hexane | HEX |
| Propyl acetate | APR | Diisopropyl ether | DIE |
| Nitromethane | NIM | Tetrahydrofuran | THF |
| Dioxane | DIX | Methanol | MOH |
| Water | $H_2O$ | Chloroform | CLF |
| 2-Butanol | BUL | Methyl acetate | MAC |
| n-Heptane | HEP | Acetone | ACE |
| Dimethylcarbonate | CDM | Methyl tert-butyl ether | MTE |
| Triethylamine | TEA | Dimethoxymethane | DMM |
| Isopropyl acetate | AIP | Dichloromethane | DCM |

In order to plan the crystallization screening, the solubility of P027 was determined at room temperature in the set of solvents of table 1 using the following methodology (table 2): 10 mg of the delivered sample were suspended at room temperature in 0.2 mL of the corresponding solvent and successive additions (initially 0.2 mL and finally 0.5 mL) of solvent until the solid was completely dissolved or up to a maximum of 8 mL were performed. After each solvent addition the suspension was vigorously stirred for 10-15 minutes and visually inspected to determine if the solid was completely dissolved. Solubility ranges are listed in table 2.

TABLE 2

Solubility of P027 in different solvents at room temperature

| Solvent | mg/mL | Solvent | mg/mL |
|---|---|---|---|
| Chloroform | >50 | Dimethylcarbonate[2] | 1-2 |
| Dimethylsulfoxide | >50 | Tetrahydrofuran | <1.2 |
| Dimethylformamide | >50 | Methyl acetate | <1.2 |
| Dichloromethane | >50 | Isobutyl acetate | <1.2 |
| Methanol | >50 | Propyl acetate | <1.2 |
| Butyl amine | >50 | Xylene | <1.2 |
| Water | >50 | Isopropyl acetate | <1.2 |
| N,N-Dimethylacetamide | 25-50 | Toluene | <1.2 |
| Nitromethane | 25-50 | Ethyl acetate | <1.2 |
| Pyridine | 25-50 | 1,1,1-Trichloroethane | <1.2 |
| Ethanol | 15-25 | Methyl isobutyl ketone | <1.2 |
| 1,2-Dichloroethane | 15-25 | Methyl tert-butyl ether | <1.2 |
| Acetonitrile[1] | 10-20 | Dimethoxymethane | <1.2 |
| n-Butanol[1] | 5-10 | Cyclohexane | <1.2 |
| Acetone | 4.0-5.0 | Chlorobenzene | <1.2 |
| Isopropanol[1] | 4.0-5.0 | n-Heptane | <1.2 |
| 2-Butanol[1] | 3-4 | n-Hexane | <1.2 |
| Methyl ethyl ketone[1] | 2-4 | Diisopropyl ether | <1.2 |
| 3-Pentanone[2] | 1-2 | Triethylamine | <1.2 |
| Dioxane[2] | 1-2 | Diethoxymethane | <1.2 |

[1]The solid was dissolved at 60° C. The solution was left at room temperature and no solid was observed.
[2]The solid was dissolved at 80° C. The solution was left at room temperature and no solid was observed.

The solvents in which P027 was insoluble were used as antisolvents (e.g. those solvents providing a solubility<1.2 mg/mL). For example, n-Heptane (HEP) and diisopropyl ether (DIE) were used as antisolvents. The other solvents were used as dissolving solvents in the different crystallization strategies assayed.

In order to cover the broadest crystallization range possible, several crystallization methodologies were employed using the solvents described in table 1. Procedures oriented to obtain the thermodynamically stable phase as well as procedures directed to obtain kinetically favored phases were used. Moreover, solvent mediated as well as solvent free crystallization procedures were assayed. A list of the crystallization procedures used in this invention is following:

Solvent evaporation at two rates at room temperature
Solvent evaporation at different temperatures: −21, 4 and 60° C.
Crystallization from hot saturated solutions at two cooling rates
Crystallization aimed to the preparation of hydrates
Crystallization by addition of an antisolvent
Crystallization by diffusion of an antisolvent
Grinding experiments
Pressure experiments
Slurry experiments In one embodiment of the present invention, the new P027 solid form, with low crystallinity or substantially amorphous, is obtained by dissolving the P027 compound in a suitable solvent or mixture of solvents and then evaporating the solvent or mixture of solvents to obtain the amorphous form. In a preferred embodiment of the present invention, the solvent is water, a mixture of water and a polar solvent, or a polar solvent. More preferably the solvent is selected from water, acetonitrile, isopropanol, methanol or a mixture comprising water such as a mixture of acetonitrile-water, isopropanol-water or methanol-water. More preferably, the solvent is water or a mixture of acetonitrile-water, isopropanol-water or methanol-water.

According to one variant of this process, the P027 compound may be dissolved at a temperature about room temperature (about 20 to about 25° C.) or above, for instance at a temperature ranging from about room temperature to about 120° C. In another variant to this process, the P027 amorphous form may be obtained when the solvent is evaporated at a temperature ranging from about 40° C. to about 60° C. Likewise, the solvent can be conveniently evaporated at about room temperature or above.

Additionally to the standard crystallization procedures, a new methodology was used applying polymers to induce the crystallization of new solids. As described in the literature, the use of polymers could favor the formation of new crystalline phases (M. Lang et al. *J. Am. Chem. Soc.*, 2002, 124, 14834; C. Price et al. *J. Am. Chem. Soc.*, 2005, 127, 5512). Moreover the presence of polymers could support the formation of larger single crystals and stabilize the formation of solvates. A series of polymers (see table 3) were added in catalytic amounts to a solution of P027 and crystallized using the following methodologies:

Solvent evaporation at room temperature
Crystallization by antisolvent addition
Crystallization from hot saturated solutions
Grinding experiments

TABLE 3

Polymers used in this invention

| Name | Code |
|---|---|
| Hydroxipropyl methyl cellulose | HPC |
| Poly(ethylene glycol) | PGY |
| Polyvinyl pyrrolidone | PVP |
| Poly(acrylic acid) | PAA |
| Nylon 6/6 | NYL |
| Polypropylene | PPL |
| Poly(styrene-co-divinylbenzene) | PSV |
| Polyvinylchloride | PVC |
| Poly(tetrafluoroethylene) | PTF |
| Poly(vinyl acetate) | PVA |
| Poly(vinyl alcohol) | PVH |
| Polyacrylamide | PAD |
| Polysulfone | PLS |
| Poly(methyl methacrilate) | PMM |

As used herein referring to polymers, "catalytic amounts" represent a substoichiometric amount of polymer with respect to the compound P027; preferably below a 25% wt of the amount of compound P027: In a particular embodiment, "catalytic amounts" represent below a 20% wt of the compound P027. In a more particular embodiment, "catalytic amounts" represent below a 10% wt of the compound P027.

In the experiments of crystallization using polymers, the solvent was selected from the above-mentioned list for the experiments without polymers. In a preferred embodiment of the present invention, when using polymers the solvent is water, a mixture of water and a polar solvent, or a polar solvent. More preferably the solvent is selected from water, acetonitrile, isopropanol, methanol or a mixture comprising water such as a mixture of acetonitrile-water, isopropanol-water or methanol-water. More preferably, solvent is water or methanol.

In the experiments of crystallization using polymers by solvent evaporation or by antisolvent addition, the P027 compound may be dissolved at a temperature about room temperature (about 20 to about 25° C.) or above, for instance at a temperature ranging from about room temperature to about 120° C. Then, the solvent can be conveniently evaporated at about room temperature or above.

In the experiments of crystallization using polymers from hot saturated solutions, the temperature may depend on the solvent used. For example, a temperature about 100° C. is suitable for water.

All solids obtained using the different crystallization methodologies were characterized by PXRD and classified according to the different PXRD patterns obtained. Further analyses performed were also taken into account for the classification of the solids. (see experimental section).

Figure 1:
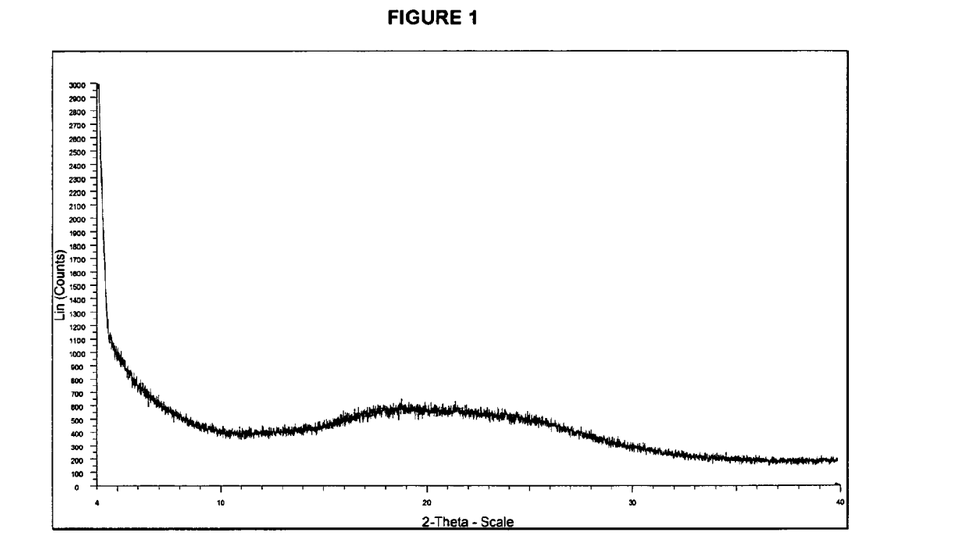
FIG. 1: Standard PXRD pattern of the amorphous phase of P027 prepared in example 1.

The standard PXRD pattern of the amorphous phase obtained is represented in FIG. 1. As expected, no peaks were observed. PXRD was used for evaluating the stability of the amorphous phase as well.

Figure 2:
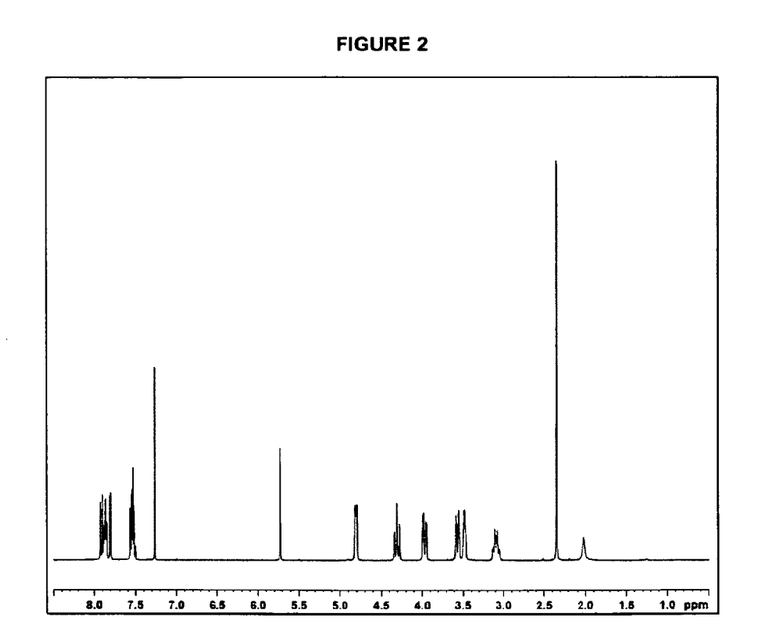
FIG. 2: $^1$H NMR spectrum of the amorphous phase of P027 prepared in example 1.

In addition, several samples of the amorphous form obtained were analyzed by $^1$H NMR in order to check the stability of the salt (FIG. 2 is a $^1$H NMR spectrum of the amorphous phase). The chemical shifts and the integrations of the $^1$H NMR signals were coincident for all samples and no signs of the lost of HCl or decomposition of the samples could be observed.

A DSC analysis of amorphous form samples was performed with a heating rate of 10° C./min. The DSC analysis presents a broad exothermic peak with an onset at 105° C. and an enthalpy of 83 $Jg^{-1}$, probably due to the lost of water overlapped with recrystallization of the sample, and a sharp endothermic peak with an onset at 194° C. and an enthalpy of 95 $Jg^{-1}$, due to the fusion of phase I followed by decomposition (see FIG. 3).

The TGA analysis of an amorphous form sample showed a weight loss of 2.4% between 40 and 140° C. Decomposition on melting of the sample was observed at temperatures higher than 190° C. (see FIG. 3).

Figure 4:
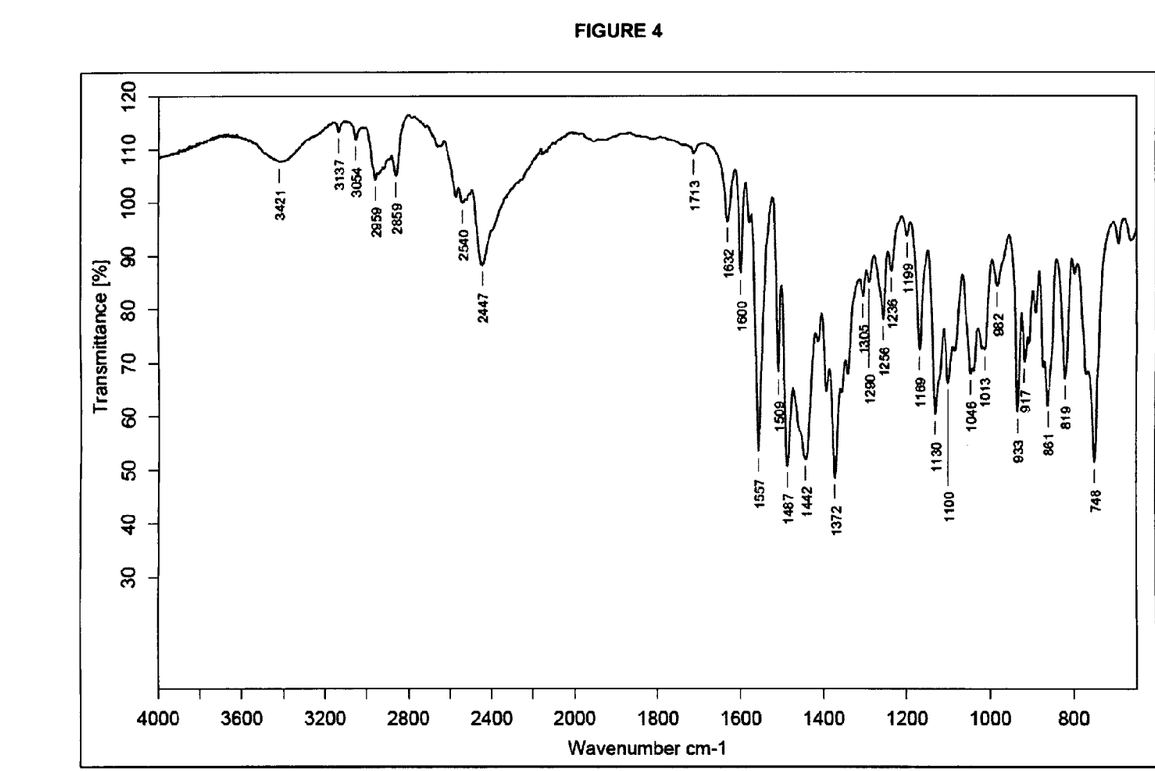
FIG. 4: FTIR analysis of the amorphous phase of P027 prepared in example 1.

The FTIR spectrum of P027 amorphous presented intense peaks at about: 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819 and 748 $cm^{-1}$ (see FIG. 4).

Another further embodiment of the present invention includes the transformation of a P027 solid form having a low degree of crystallinity, including substantially amorphous forms, into a more stable polymorphic form such as phase I form.

A further embodiment of the present invention includes pharmaceutical compositions comprising the above-mentioned solid forms of the hydrochloride salt of 4-[2-[[5-methyl-1-(2-naphthalenyl)-1H-pyrazol-3-yl]oxy]ethyl]morpholine.

Having described the invention in general terms, it will be more easily understood by reference to the following examples which are presented as an illustration and are not intended to limit the present invention.

EXAMPLES

Equipment used in the characterization of 4-[2-[[5-methyl-1-(2-naphthalenyl)-1H-pyrazol-3-yl]oxy]ethyl]morpholine hydrochloride amorphous form.

a) Powder X-ray Diffraction Analysis (PXRD)

Approximately 20 mg of the non manipulated samples were prepared in standard sample holders using two foils of polyacetate.

Powder diffraction patterns were acquired on a D8 Advance Series 2Theta/Theta powder diffraction system using $Cu_{K\alpha}$-radiation in transmission geometry (Wavelength: 1.54060 Å). The system was equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.5.1 and evaluation with EVA V.12.0.

b) Proton Nuclear Magnetic Resonance ($^1$H NMR)

Proton nuclear magnetic resonance analyses were recorded in deuterated chloroform (CDCl$_3$) in a Bruker Avance 400 Ultrashield NMR spectrometer, equipped with a z-gradient 5 mm BBO (Broadband Observe) probe with ATM and an automatic BACS-120 autosampler. Spectra were acquired solving 2-10 mg of sample in 0.6 mL of deuterated solvent.

c) Differential Scanning Calorimetry Analysis (DSC)

Standard DSC analyses were recorded in a Mettler Toledo DSC822e. Samples of 1-2 mg were weighted into 40 μL aluminum crucibles with a pinhole lid, and were heated, under nitrogen (50 mL/min), from 30 to 300° C. at 10° C./min. Data collection and evaluation was done with software STARe.

d) Thermogravimetric Analysis (TGA)

Thermogravimetric analyses were recorded in a Mettler Toledo SDTA851e. Samples of 3-4 mg were weighted (using a microscale MX5, Mettler) into open 40 μL aluminum crucibles with a pinhole lid, and heated at 10° C./min between 30 and 500° C., under nitrogen (80 mL/min). Data collection and evaluation was done with software STARe.

e) Fourier Transform Infrared Analysis (FTIR)

The FTIR spectra were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$. No sample preparation was required to perform the analysis.

Example 1

Preparation and Characterization of P027 Amorphous Form 0.2 g of compound P027 was dissolved in 4.8 mL of water at room temperature. The resulting solution was left to evaporate in a Petri plate at 60° C. The resulting oil solidified and the solid obtained was analyzed by PXRD, $^1$H NMR, DSC, TGA, FTIR and KF.

P027 amorphous form was also prepared with solvent mixtures comprising water. The solutions were prepared from 20 mg of compound P027 in 0.2 ml of the solvent/water mixture at 60° C. The ratio of the solvents used and the crystallization time was respectively:

Acetonitrile/H$_2$O 75/25 for 1 month;
Isopropanol/H$_2$O 25/75 for 1 month; and
Methanol/H$_2$O 50/50 and 25/75 for 1 month.
K.F. analysis: 3.6±0.1% (theoretical 3.04%).

The characterisation of P027 amorphous form is the following (FIGS. 2-4):

$^1$H NMR (400 MHz, CDCl$_3$): δ 2.35 (s, 3H), 3.04-3.13 (m, 2H), 3.46-3.50 (m, 2H), 3.56 (d, J=12 Hz, 2H), 3.97 (dd, J=13 Hz, J=3 Hz, 1H), 4.27-4.34 (m, 2H), 4.79-4.82 (m, 2H), 5.73 (s, 1H), 7.49-7.57 (m, 3H), 7.80-7.92 (m, 4H) ppm.

Figure 3:
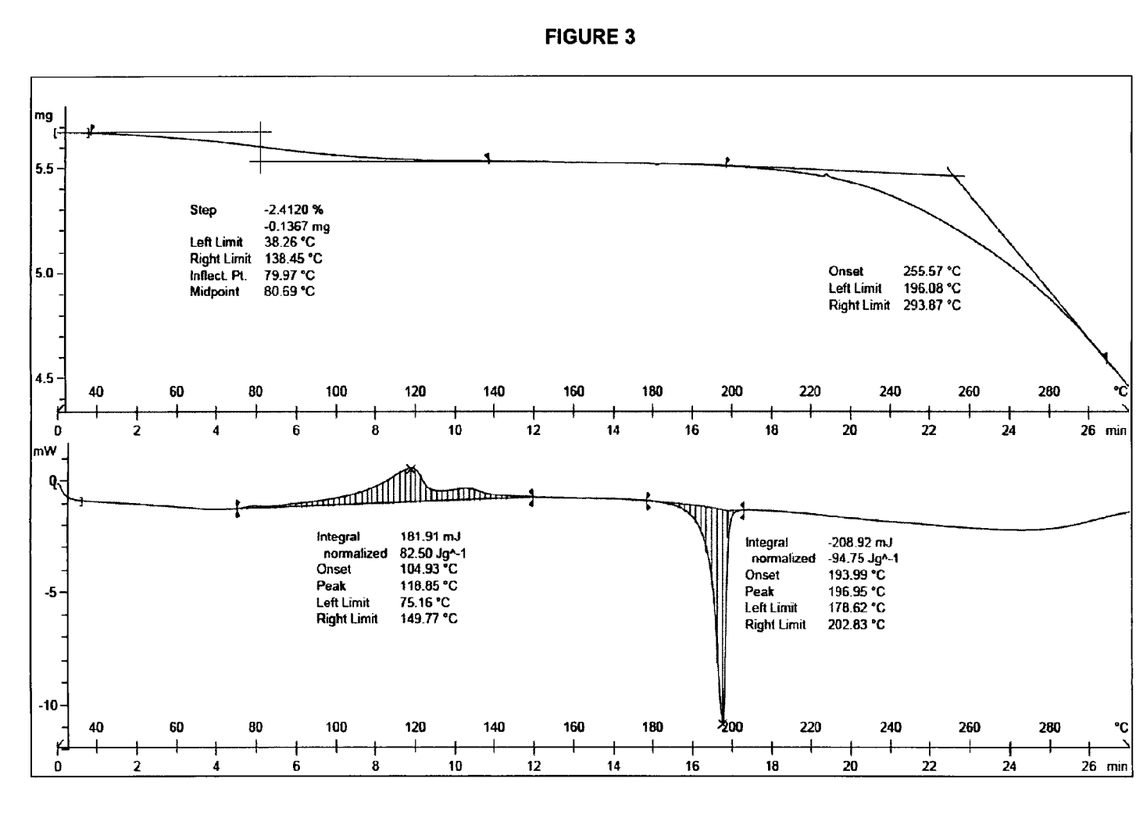
FIG. 3: DSC and TGA analyses of the amorphous phase of P027 prepared in example 1.

DSC (10° C./min): The DSC analysis presents a broad exothermic peak with an onset at 105° C. and an enthalpy of 83 Jg$^{-1}$, probably due to the lost of water overlapped with recrystallization of the sample, and a sharp endothermic peak with an onset at 194° C. and an enthalpy of 95 Jg$^{-1}$, due to the fusion of phase I followed by decomposition.

TGA (10° C./min): A weight loss in the range between 40 and 140° C. of 2.4% and a weight loss starting at around 190° C. corresponding to decomposition on melting.

FTIR (ATR): 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819 and 748 cm$^{-1}$.

The scale-up of the amorphous phase was performed by evaporation of a solution in water of P027 at higher temperatures using 100, 200, 300 and 500 mg of compound. The results obtained in each case are gathered in table 4.

TABLE 4

Scale-up of the amorphous phase

| Entry | Scale[1] | N° exp. | Procedure | Solvent | Observations |
|---|---|---|---|---|---|
| 1 | 100 mg | 1 | Solvent evaporation at 40° C. | water | amorphous |
| 2 | 100 mg | 1 | Solvent evaporation at 50° C. | water | amorphous |
| 3 | 100 mg | 1 | Solvent evaporation at 60° C. | water | amorphous |
| 4 | 200 mg | 4 | Solvent evaporation at 60° C. | water | amorphous |
| 5 | 300 mg | 5 | Solvent evaporation at 60° C. | water | amorphous |

[1]Referred to starting compound P027.

In the scale up, the experiments performed at 100, 200 and 300 mg scale, gave the amorphous phase.

Example 2

Stability Evaluation of the P027 Amorphous Form Obtained

In order to test the stability of the amorphous phase and to investigate its stability, different portions of the amorphous phase were dried for four hours at different temperatures (table 5). Once the samples were dried the solid was analyzed by PXRD. In the drying experiments performed at temperatures up to 60° C. for four hours, amorphous phase was recovered. At temperatures over 60° C., the amorphous phase transformed slightly to a crystalline phase, not clearly identified. After drying for four hours at temperature higher than 100° C. the amorphous phase transformed clearly to phase I.

TABLE 5

Results for the drying experiments of the amorphous phase

| Code | Temperature (° C.) | Solid phase |
|---|---|---|
| Sample 1 | rt | amorphous |
| Sample 2 | 40 | amorphous |
| Sample 3 | 50 | amorphous |
| Sample 4 | 60 | amorphous |
| Sample 5 | 80 | amorphous + crystalline |
| Sample 6 | 90 | amorphous + crystalline |
| Sample 7 | 100 | phase I + crystalline |
| Sample 8 | 110 | phase I |
| Sample 9 | 120 | phase I |

In a second experiment, different portions of the amorphous phase were dried under vacuum conditions (5-7 mbar) at room temperature, 40° C. and 60° C. for different times (4, 8, 16 and 24 hours; table 6). Once the samples were dried, the solid was analyzed by PXRD. In the experiments performed under vacuum at room temperature the amorphous phase did not change after drying. In the experiments performed at 40° C. the amorphous phase began to crystallize after 16 hours. In the experiments performed at 60° C. the amorphous phase began to crystallize after 8 hours and phase I could be clearly identified after 16 hours.

TABLE 6

Results for the drying experiments of the amorphous phase

| Code | Time (hours) | Solid phase |
|---|---|---|
| 23° C. | | |
| Sample 10 | 4 | amorphous |
| Sample 11 | 8 | amorphous |
| Sample 12 | 16 | amorphous |
| Sample 13 | 24 | amorphous |
| 40° C. | | |
| Sample 14 | 4 | amorphous |
| Sample 15 | 8 | amorphous |
| Sample 16 | 16 | amorphous + phase I |
| Sample 17 | 24 | amorphous + phase I |
| 60° C. | | |
| Sample 18 | 4 | amorphous |
| Sample 19 | 8 | amorphous + phase I |
| Sample 20 | 16 | phase I |
| Sample 21 | 24 | phase I |

Example 3

Crystallization Screening using Catalytic Amounts of Polymers for Obtained the Amorphous Form Selection of Polymers With the aim to induce the formation of new crystalline forms of P027, catalytic amounts of polymers were added to the crystallization experiments. The polymers used are listed in table 3.

Solvent Evaporation at Room Temperature

Samples of P027 (20-25 mg) were dissolved in the minimum amount of the corresponding solvent at room temperature and a small quantity of polymer (4-5 mg) was added to the corresponding solution (tables 7 and 8). The resulting solutions or suspensions were left to evaporate in open vials at room temperature. All solid samples were analyzed by PXRD.

TABLE 7

Results from fast evaporation experiments at room temperature with water

| Polymer | V (mL) | PXRD pattern |
|---|---|---|
| Hydroxipropyl methyl cellulose | 0.7 | amorphous |
| Polyvinyl pyrrolidone | 0.7 | amorphous |
| Poly(acrylic acid) | 0.7 | amorphous |
| Poly(styrene-co-divinylbenzene) | 0.7 | amorphous |
| Polyvinylchloride | 0.7 | amorphous |
| Polyacrilamide | 0.7 | amorphous |
| Polysulfone | 0.7 | amorphous |

TABLE 8

Results from fast evaporation experiments at room temperature with methanol

| Polymer | V (mL) | PXRD pattern |
|---|---|---|
| Hydroxipropyl methyl cellulose | 0.7 | amorphous |
| Polyacrilamide | 0.7 | amorphous |
| Polysulfone | 0.7 | amorphous |

Crystallization by Addition of an Antisolvent

Diisopropyl ether (DIE) was selected as antisolvent for the crystallization experiments by addition of an antisolvent. Samples of P027 (20-25 mg) with the corresponding polymer (5-6 mg) were dissolved in the minimum amount of the dissolving solvent at room temperature and the antisolvent was added under vigorous stirring (table 9). When solids were obtained after antisolvent addition, they were separated by centrifugation. If not, the solution was left to evaporate at room temperature. The solids obtained were analyzed by PXRD.

TABLE 9

Results from crystallization experiments in water by addition of an antisolvent

| Polymer | Crystallization | PXRD |
|---|---|---|
| Poly(acrylic acid) | Evaporation | amorphous |
| Poly(styrene-co-divinylbenzene) | Evaporation | amorphous |
| Polyvinylchloride | Evaporation | amorphous |
| Poly(vinyl alcohol) | Evaporation | amorphous |
| Polyacrilamide | Evaporation | amorphous |

Crystallization from Hot Saturated Solutions

Samples with P027 (20-30 mg) and the corresponding polymer (4-5 mg) were dissolved in the minimum amount of the corresponding solvent at high temperature to obtain a saturated solution and slowly cooled to room temperature (table 10). When solids were obtained after cooling at room temperature, they were separated by centrifugation. If not, the solutions were left evaporating up to dryness at room temperature. All the solids obtained were analyzed by PXRD.

TABLE 10

Results from crystallization experiments from hot saturated solutions in water at 100° C.

| Polymer | V (mL) | Crystallization conditions | PXRD pattern |
|---|---|---|---|
| Hydroxipropyl methyl cellulose | 0.2 | Evaporation | amorphous |
| Nylon 6/6 | 0.2 | Evaporation | amorphous |
| Poly(styrene-co-divinylbenzene) | 0.2 | Evaporation | amorphous |
| Polyvinylchloride | 0.2 | Evaporation | amorphous |
| Poly(tetrafluoroethylene) | 0.2 | Evaporation | amorphous |
| Poly(vinyl acetate) | 0.2 | Evaporation | amorphous |
| Poly(vinyl alcohol) | 0.2 | Evaporation | amorphous |
| Polyacrilamide | 0.2 | Evaporation | amorphous |
| Polysulfone | 0.2 | Evaporation | amorphous |
| Poly(methyl methacrilate) | 0.2 | Evaporation | amorphous |

The invention claimed is:

1. A process for preparing a substantially amorphous solid form of a hydrochloride salt of 4-[2-[[5-methyl-1-(2-naphthalenyl)-1H-pyrazol-3-yl]oxy]ethyl]morpholine, wherein the substantially amorphous solid form has an X-ray powder diffraction pattern showing no characteristic peaks, the process comprising:
   a) dissolving the hydrochloride salt of 4-[2-[[5-methyl-1-(2-naphthalenyl)-1H-pyrazol-3-yl]oxy]ethyl]morpholine in a suitable solvent or mixture of solvents, and
   b) evaporating the solvent or mixture of solvents,
      wherein the solvent or mixture of solvents is selected from the group consisting of water, acetonitrile, isopropanol, methanol, acetonitrile-water, isopropanol-water, and methanol-water.

2. The process according to claim 1, wherein said dissolving is performed at a temperature ranging from about room temperature to 120° C.

3. The process according to claim 1, wherein said evaporating of the solvent or mixture of solvents is performed at a temperature of about room temperature or above.

4. A process for preparing the substantially amorphous solid form according to claim 1, wherein the solid form has a FTIR spectrum showing characteristic peaks at about: 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819, and 748 $cm^{-1}$.

5. A process for preparing a substantially amorphous solid form of a hydrochloride salt of 4-[2-[[5-methyl-1-(2-naphthalenyl)-1H-pyrazol-3-yl]oxy]ethyl]morpholine, wherein the substantially amorphous solid form has an X-ray powder diffraction pattern showing no characteristic peaks, the process comprising one of the following steps (i) to (iii):
 i) a) dissolving the hydrochloride salt of 4-[2-[[5-methyl-1-(2-naphthalenyl)-1H-pyrazol-3-yl]oxy]ethyl]morpholine in a suitable solvent or mixture of solvents in the presence of catalytic amounts of at least one polymer selected from the group consisting of: hydroxypropyl methyl cellulose, polyvinyl pyrrolidone, poly(acrylic acid), poly(styrene-co-divinylbenzene), polyvinylchloride, polyacrylamide, and polysulfone; and b) evaporating the solvent or mixture of solvents;
 (ii) a) dissolving the hydrochloride salt of 4-[2-[[5-methyl-1-(2-naphthalenyl)-1H-pyrazol-3-yl]oxy]ethyl]morpholine in a suitable solvent or mixture of solvents in the presence of catalytic amounts of at least one polymer selected from the group consisting of: poly(acrylic acid), poly(styrene-co-divinylbenzene), polyvinylchloride, poly(vinyl alcohol), and polyacrylamide; and b) adding diisopropyl ether as an antisolvent; and
 (iii) crystallizing the hydrochloride salt of 4-[2-[[5-methyl-1-(2-naphthalenyl)-1H-pyrazol-3-yl]oxy]ethyl]morpholine from a hot saturated solution of a suitable solvent or mixture of solvents in the presence of catalytic amounts of at least one polymer selected from the group consisting of: hydroxypropyl methyl cellulose, nylon 6/6, poly(styrene-co-divinylbenzene), polyvinylchloride, poly(vinyl acetate), poly(vinyl alcohol), polyacrylamide, polysulfone and poly(methyl methacrylate);

wherein the solvent or mixture of solvents is selected from the group consisting of: water, acetonitrile, isopropanol, methanol, acetonitrile-water, isopropanol-water, and methanol-water.

6. A process for preparing the substantially amorphous solid form according to claim 5, wherein the solid form has a FTIR spectrum showing characteristic peaks at about: 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819, and 748 $cm^{-1}$.

7. A method comprising use of a substantially amorphous solid form of a hydrochloride salt of 4-[2-[[5-methyl-1-(2-naphthalenyl)-1H-pyrazol-3-yl]oxy]ethyl]morpholine according to claim 1, wherein the substantially amorphous solid form has an X-ray powder diffraction pattern showing no characteristic peaks, as an intermediate for preparing crystalline form phase I of a hydrochloride salt of 4-[2-[[5-methyl-1-(2-naphthalenyl)-1H-pyrazol-3-yl]oxy]ethyl]morpholine, the method comprising a step of drying said substantially amorphous solid form.

8. A method according to claim 7, wherein the solid form has a FTIR spectrum showing characteristic peaks at about: 3421, 3137, 3054, 2959, 2859, 2540, 2447, 1632, 1600, 1557, 1509, 1487, 1442, 1372, 1305, 1290, 1256, 1236, 1199, 1169, 1130, 1100, 1046, 1013, 982, 933, 917, 861, 819, and 748 $cm^{-1}$.

9. The method of claim 7, wherein the drying comprises:
 (a) drying the solid form for at least four hours at a temperature of at least 100° C.;
 (b) drying the solid form under vacuum conditions for at least 16 hours at a temperature of at least 40° C.; or
 (c) drying the solid form under vacuum conditions for at least 8 hours at a temperature of at least 60° C.

10. The method of claim 8, wherein the drying comprises:
 (a) drying the solid form for at least four hours at a temperature of at least 100° C.;
 (b) drying the solid form under vacuum conditions for at least 16 hours at a temperature of at least 40° C.; or
 (c) drying the solid form under vacuum conditions for at least 8 hours at a temperature of at least 60° C.

\* \* \* \* \*